(12) United States Patent
Jones et al.

(10) Patent No.: US 12,090,280 B2
(45) Date of Patent: *Sep. 17, 2024

(54) APPARATUS FOR ADMINISTERING BILATERAL TACTILE STIMULATION TO A HUMAN SUBJECT

(71) Applicant: Bi-Tapp, Inc., St. George, UT (US)

(72) Inventors: Cindy Ann Jones, Cedar City, UT (US); Hayley B. Taylor, St. George, UT (US); Martin Robert Johnson, Draper, UT (US); Jeremy Paul Willden, Pleasant Grove, UT (US); Helaman David Pratt Ferguson, Orem, UT (US); Phillip Wayne Dietz, St. George, UT (US)

(73) Assignee: NI-Tapp, Inc., St. George, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/187,602

(22) Filed: Mar. 21, 2023

(65) Prior Publication Data

US 2023/0277801 A1 Sep. 7, 2023

Related U.S. Application Data

(63) Continuation of application No. 17/087,322, filed on Nov. 2, 2020, now Pat. No. 11,607,521, which is a (Continued)

(51) Int. Cl.
*A61M 21/02* (2006.01)
*A61M 21/00* (2006.01)
(Continued)

(52) U.S. Cl.
CPC ..... *A61M 21/02* (2013.01); *A61M 2021/0022* (2013.01); *A61M 2205/3553* (2013.01);
(Continued)

(58) Field of Classification Search
None
See application file for complete search history.

(56) References Cited

U.S. PATENT DOCUMENTS

2018/0177975 A1* 6/2018 Goto ............... A61B 5/4818

* cited by examiner

*Primary Examiner* — Thaddeus B Cox
(74) *Attorney, Agent, or Firm* — Gurr Brande & Spendlove, PLLC; Robert A. Gurr

(57) ABSTRACT

This invention generally provides two tactile stimulation modules, or "tappers". One tapper is held by a person in each of his hands. Alternatively, a tapper is secured to each wrist or to other parts of the body on opposite sides. Each tapper is powered by a rechargeable battery, and contains both a tactile stimulation transducer, such as an electric motor having either a balanced or unbalanced mass on its output shaft, and a transceiver that communicates with a host or master. Each tapper includes at least one control button and a status indicator. Each tapper contains a micro-controller that performs tasks such as communication, motor activation, user monitoring and control, battery monitoring, low-power sleep, and algorithm execution. At least one tapper can contain at least one optional sensor, which measures a physiological function. Measurements can be used to modify performance of the tactile stimulation transducers.

3 Claims, 14 Drawing Sheets

Related U.S. Application Data continuation of application No. 15/970,870, filed on May 3, 2018, now Pat. No. 10,821,261.

(60) Provisional application No. 62/501,736, filed on May 4, 2017.

(51) Int. Cl.
*G16H 40/63* (2018.01)
*G16H 40/67* (2018.01)
*G16H 50/20* (2018.01)

(52) U.S. Cl.
CPC ............... *A61M 2205/3584* (2013.01); *A61M 2205/3592* (2013.01); *A61M 2205/505* (2013.01); *A61M 2205/583* (2013.01); *A61M 2205/8206* (2013.01); *A61M 2209/088* (2013.01); *A61M 2230/04* (2013.01); *A61M 2230/10* (2013.01); *A61M 2230/205* (2013.01); *A61M 2230/42* (2013.01); *A61M 2230/432* (2013.01); *A61M 2230/50* (2013.01); *A61M 2230/60* (2013.01); *A61M 2230/65* (2013.01); *G16H 40/63* (2018.01); *G16H 40/67* (2018.01); *G16H 50/20* (2018.01)

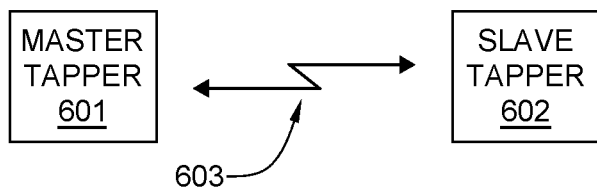
FIG. 6
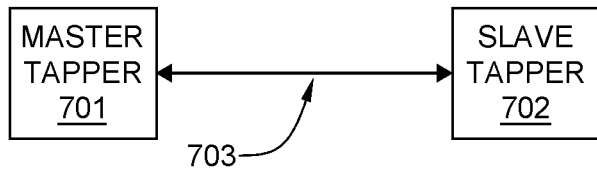
FIG. 7
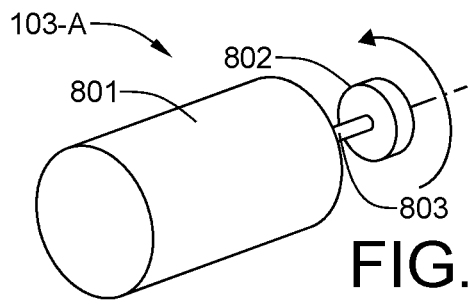
FIG. 8
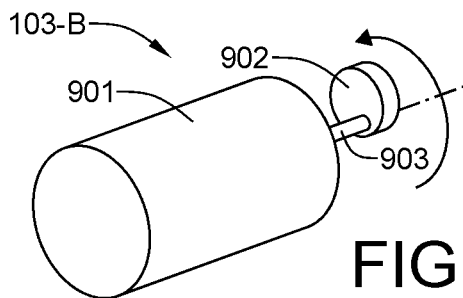
FIG. 9
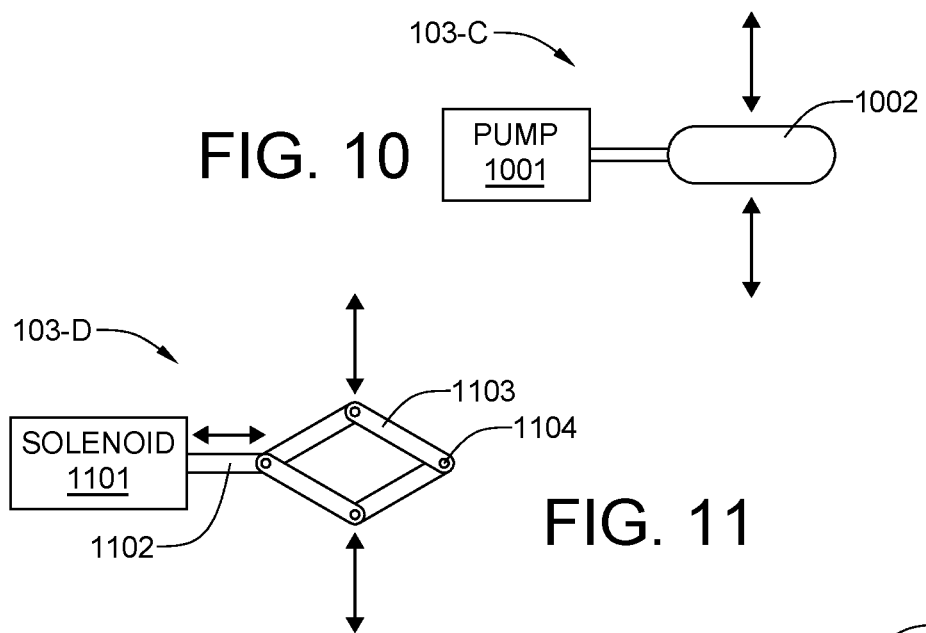
FIG. 10
FIG. 11
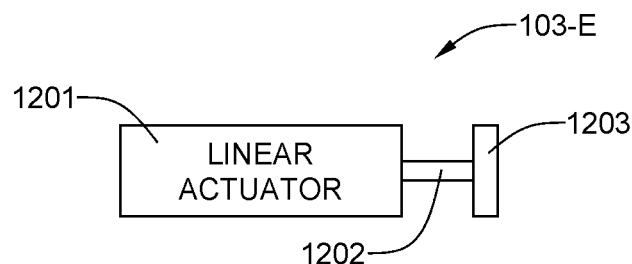
FIG. 12

APPARATUS FOR ADMINISTERING BILATERAL TACTILE STIMULATION TO A HUMAN SUBJECT

CROSS-REFERENCE TO RELATED APPLICATIONS

This application is a continuation of U.S. patent application Ser. No. 17/087,322, filed on Nov. 2, 2020, now U.S. Pat. No. 11,607,521, which was a continuation of U.S. patent application Ser. No. 15/970,870, filed on May 3, 2018, now U.S. Pat. No. 10,821,261, which claimed the benefit of U.S. Provisional Application Ser. No. 62/501,736, filed on May 4, 2017, all of which are incorporated herein by reference.

TECHNICAL FIELD

This invention relates, generally, to apparatuses for providing tactile stimulation to human subjects in connection with psychotherapy and, more particularly, to devices for administering bilateral tactile stimulation to a human subject in order to elicit a calming effect on the subject.

BACKGROUND

In 1987, psychologist Dr. Francine Shapiro made the chance observation that eye movements can reduce the intensity of disturbing thoughts, under certain conditions. Dr. Shapiro studied this scientifically, and in a 1989 issue of the Journal of Traumatic Stress, she reported success using EMDR (Eye Movement Desensitization and Reprocessing) to treat victims of trauma. Since then, EMDR therapy has developed and evolved through the contributions of therapists and researchers all over the world. EMDRIA (EMDR International Association) states that EMDR therapy is a set of standardized protocols that incorporate many elements from many different treatment approaches. Scientific research has established EMDR therapy as an effective treatment for posttraumatic stress disorder. Success has also been found in the treatment of many other conditions such as: pain attacks, dissociative disorders, pain disorders, addictions, sexual and/or physical abuse and stress reduction.

An EMDR therapist is going to be taught to utilize Eye Movement Bilateral Stimulation as their first choice when working with clients. There are exceptions to using this modality such as: a client has difficulty tracking eye movements due to blindness or a young child may not be able to sustain attention to follow the therapist's fingers. A client also may begin to cry intensely enough that it is difficult to track the bilateral eye movements. As a result of this, a therapist may switch to tactile bilateral stimulation or bilateral tones so that the reprocessing may continue. In addition to possible limitations or issues that the client may have, the therapist might also have physical limitations or struggle with fatigue if seeing several clients in one day.

In response to the needs of providing alternatives to the therapist manually providing bilateral eye movement, devices have been developed to assist therapists in their work. On Aug. 30, 1994, U.S. Pat. No. 5,343,261, which disclosed a device for inducing saccadic eye movements, issued to David L. Wilson. The device also included an option for utilizing bilateral tones. On Dec. 14, 1999, U.S. Pat. No. 6,001,073, which disclosed a device for inducing alternating tactile stimulations, was issued to Jurgen G. Schmidt and Shirley Jean Schmidt. In an effort to reduce strain on their shoulders, therapists have also utilized wants to facilitate the bilateral eye movements for clients.

In addition to these devices used in therapy, the "butterfly hug" method was originated and developed by Lucina Artigas during her work with the survivors of Hurricane Pauline in Acapulco, Mexico, 1998. Artigas and Ignacio Jarero have utilized this method when working with survivors of man-made and natural catastrophes around the world. Instead of the clinicians being in charge of the bilateral stimulation, clients are asked to do the butterfly hug during the reprocessing phases 4 to 6.

In the book, Getting Past Your Past, Dr. Francine Shapiro discusses how to use bilateral tapping as a resource. She states, "Here are two kinds of stimulation you can use", she says. "One is just putting your hands on your thighs and tapping first one and then the other. If bilateral stimulation helps, then use it daily." She also teaches the butterfly hug. "As long as you were able to use it successfully, you can also try it when you're feeling stressed or anxious." Individuals are taught that if negative associations begin to emerge through the use of these techniques, they should stop using them and instead use other self-control techniques, such as breathing techniques.

There are many resources now available which are designed to assist the general public in utilizing visual, auditory, and bilateral tactile stimulation as a way to reduce stress and anxiety. Software programs and applications have been developed for bilateral eye movement. Bilateral tones and bilateral music have also been created and can be found on applications programs for mobile devices as well as in music stores.

In 2016, Dr. Amy Serin and Vicki Mayo formed a limited liability company named VMAS Solutions LLC and jointly developed a handheld and wearable tactile stimulation product that was originally sold under the Buzzies mark, but is now being sold under the Touchpoint mark. The product comprises a pair of wrist wearable devices that alternately provide a buzzing tactile sensation to opposite sides of the body.

The same issues that emerged in a therapy office are emerging as the same techniques that are being taught to the general public as a way to reduce stress and enhance positive resources. All three modalities need to be offered to individuals (bilateral eye movements, tones and bilateral tapping). Someone might have a hearing impairment. There will be those who cannot manually perform the bilateral tapping due to age or disabilities. Some people who can perform bilateral tapping on themselves, might become fatigued or distracted. Children are not going to be able to sustain the bilateral tapping for an extended period of time What is needed is a wireless electro-mechanical product that replicates bilateral tapping and closely mimics the sensation of human touch with only an initial set-up so that the user may move around freely. Ideally, the product would use bio-feedback to automatically adjust the stimulation parameters without the need for continual manual intervention from either the user or the therapist, thereby increasing the effectiveness of this modality whether it is used in a clinical setting or for private use. Lastly, the product would preferably record the usage pattern so that it can be reviewed by the user, his mental health therapist or his medical provider.

SUMMARY OF EXAMPLE EMBODIMENTS

The present invention generally provides a pair of tactile stimulation modules. The modules are also called "tappers".

One tapper is held in the right hand, the other in the left hand. Alternatively, for those individuals who are unable to easily grasp objects with the hands, or who can benefit from the bilateral therapy while performing other manual tasks, can strap a tapper—much like a wrist watch—to each wrist. A further alternative is to wear the tappers elsewhere on the body. For example, they may be worn on the ankles by holding them in place with the upper portion of socks. Finally, the tappers can be worn yet elsewhere, such as on a band around the waist or chest.

Each tapper is battery powered. Each contains a tactile stimulation transducer, such as an electric motor having either a balanced mass or an unbalanced mass on the output shaft. In addition, each tapper contains a means of wireless communication with a host or master. Moreover, each tapper contains a means of user interaction so that the user can activate (via a button) it and view its status (via an LED indicator). Further still, each tapper may have a means of connecting an optional strap for attaching it to the wrist or ankle. At the core of each tapper, resides a micro-controller that performs such useful tasks as: communication, activating the motor, user monitoring and control, battery monitoring, low-power sleep, executing algorithms, etc. Each tapper also contains a means of charging its battery, such as a connector or an electromagnetically coupled element. Finally, for a preferred embodiment of the invention, at least one of the two tappers contains at least one sensor, which has the ability to measure at least one physiological function. Alternatively, the sensor can be separate from the tapper. Exemplary measurements of physiological functions include pulmonary (heart) rate, respiratory breathing rate, temperature, muscle activity, skin electrical activity, brain electrical activity, blood flow in fingers and toes, heart electrical activity, brain blood flow, oxygenation levels of blood in the brain, exhaled $CO_2$ levels, oxygen saturation levels in the bloodstream, and muscle tightness.

Wireless communication between the tappers and the host can be any wireless communication protocol whether it be a standard protocol, such as Bluetooth® or Wi-Fi, or whether it be a proprietary wireless communication method. The present implementation uses Bluetooth, as that protocol is generally supported by most smartphones and tablets. Bluetooth is a wireless technology standard for exchanging data over short distances, using short-wavelength UHF radio waves in the ISM band from 2.4 to 2.4835 GHz, from fixed and mobile devices. Invented by telecom vendor Ericsson in 1994, it was originally conceived as a wireless alternative to RS-232 data cables. Although the Institute of Electrical and Electronic Engineers (IEEE) created the Bluetooth standard as IEEE specification 802.15.1, it no longer maintains it. Instead, it is now managed by the Bluetooth Special Interest Group (SIG), which has more than 30,000 member companies working in the fields of telecommunication, computing, networking, and consumer electronics. The Bluetooth SIG currently oversees development of the specification, manages the qualification program, and protects the trademarks. A manufacturer must meet Bluetooth SIG standards to market it as a Bluetooth device.

The tappers can operate in a mode where they use bio-feedback and a control algorithm to automatically adjust the parameters that dictate the tapping regime. The bio-feedback control algorithm is designed to help a person achieve a deeper level of biostasis more rapidly and/or for a longer period of time.

Unlike other bilateral tactile stimulation devices that are presently being marketed, which rely on a buzzing sensation produced by an unbalanced mass on the output shaft of an electric motor, the tappers of the present invention are designed to produce tactile stimulation that has the ability to substantially mimic human touch. For a preferred embodiment of the invention, each tactile stimulation device is equipped with an electric motor having a balanced mass on its output shaft. If the motor is properly balanced, such a device will not buzz, no matter how long in duration an electrical pulse is applied to the motor inputs. A tapping sensation is achieved by accelerating and decelerating the balanced mass. When a full power pulse is applied to the motor's electrical inputs, a rotational force is applied to the motor armature and balanced mass on the output shaft, resulting in an opposite and equal rotational force, in accordance with Newton's laws. This opposite and equal rotational force is perceived as a tap by the wearer of the device. As long as the armature is accelerating, an opposite and equal rotational force is being applied to the motor coils, motor housing, and the structure supporting motor (i.e., nearly the entire tactile stimulation module), which creates the sensation of a tap. Between taps, the motor armature can be slowed quickly either by reversing the power applied to the motor inputs or by shorting the motor inputs to create a braking action. Both such actions can be applied gradually so as to prevent the sensation of a secondary tap as the armature returns to rest.

For another embodiment of the invention, each tactile stimulation device is equipped with an electric motor having an unbalanced mass on its output shaft. Although such a device is not optimally designed to produce a tapping sensation, such motors are readily available at low cost. Buzzing, which is an unwanted artifact of the motor design, can either be eliminated or severely minimized by shortening the duty cycles of the motor so that the armature is accelerated through no more than one full revolution, or 360 degrees and, preferably, through no more than one half revolution, or 180 degrees. Thus, when full power is applied to the motor electrical inputs, an opposite and equal rotational force is generated that is applied to the motor coils, motor housing, and the structure supporting motor (i.e., nearly the entire tactile stimulation module), which creates the sensation of a tap. That opposite and equal force is conducted to the skin of the individual and the nerve endings thereunder. With the acceleration of the motor armature limited to no more than 360 degrees, only one vibrational pulse, at most, is driven, and that pulse will be closely associated in time with the reverse torque pulse. Thus, a person undergoing therapy will perceive the reverse torque force and the no more than one driven vibrational pulse, which is virtually contemporaneous with the reverse torque force, as a single tap. Given that an off-balance motor operates as an effective energy sink, with rotational energy being rapidly converted to vibrational energy, any residual vibrational energy decays rapidly as soon as the power pulse ends. Because the residual vibration is decaying rapidly, the reverse torque force is perceived as the dominant force by the person receiving therapy. At the high end of the 360-degree driven range, the decaying vibration is, of course, more noticeable. Therefore, if acceleration of the motor armature is limited to no more than 360 degrees, a motor having an off balance mass on its output shaft can function in a nearly identical manner as a motor equipped with a balanced mass on its output shaft. In addition, rotation of the motor armature can be braked as heretofore described for a motor with the balanced mass affixed to the output shaft. Thus, a tapping sensation can thus be achieved with either type of motor (balanced or unbalanced), although operating parameters are more restricted when using an unbalanced vibratory motor.

The technology of the present invention can be extended to a social media context. For example, it is contemplated that data derived from the sensors and tapper sessions may, at the option of the user, be published to one or more social media sites, and even shared with members of a support group or with the therapist, thereby enabling others to support the user in his/her therapy. This data can be published real-time, such as during a group therapy discussion session, or it can be published after the fact. Records of tapper sessions can be reviewed by the user, as well as by others who are given review privileges by the user.

BRIEF DESCRIPTION OF THE DRAWINGS

FIG. 6 is a block diagram of a first autonomous tapper system, in which neither tapper is connected to a host device, and the master tapper and slave tapper communicate with each other wirelessly;

FIG. 7 is a block diagram of a second autonomous tapper system, in which neither tapper is connected to a host device, and the master tapper and slave tapper communicate with each other via an electrical cable;

FIG. 8 is an isometric view of an electric motor having a balanced mass on its output shaft;

FIG. 9 is an isometric view of a motor having an unbalanced mass on its output shaft;

FIG. 10 is a schematic diagram of a bladder and a pump, whereby the pump inflates and deflates the bladder to induce tactile stimulation in a tapper;

FIG. 11 is a schematic diagram of a solenoid and an array of hinged elements used to induce tactile stimulation in a tapper;

FIG. 12 is a schematic diagram of a linear actuator and a pressure plate used to induce tactile stimulation in a tapper;

DETAILED DESCRIPTION OF EXAMPLE EMBODIMENTS

Figure 1:
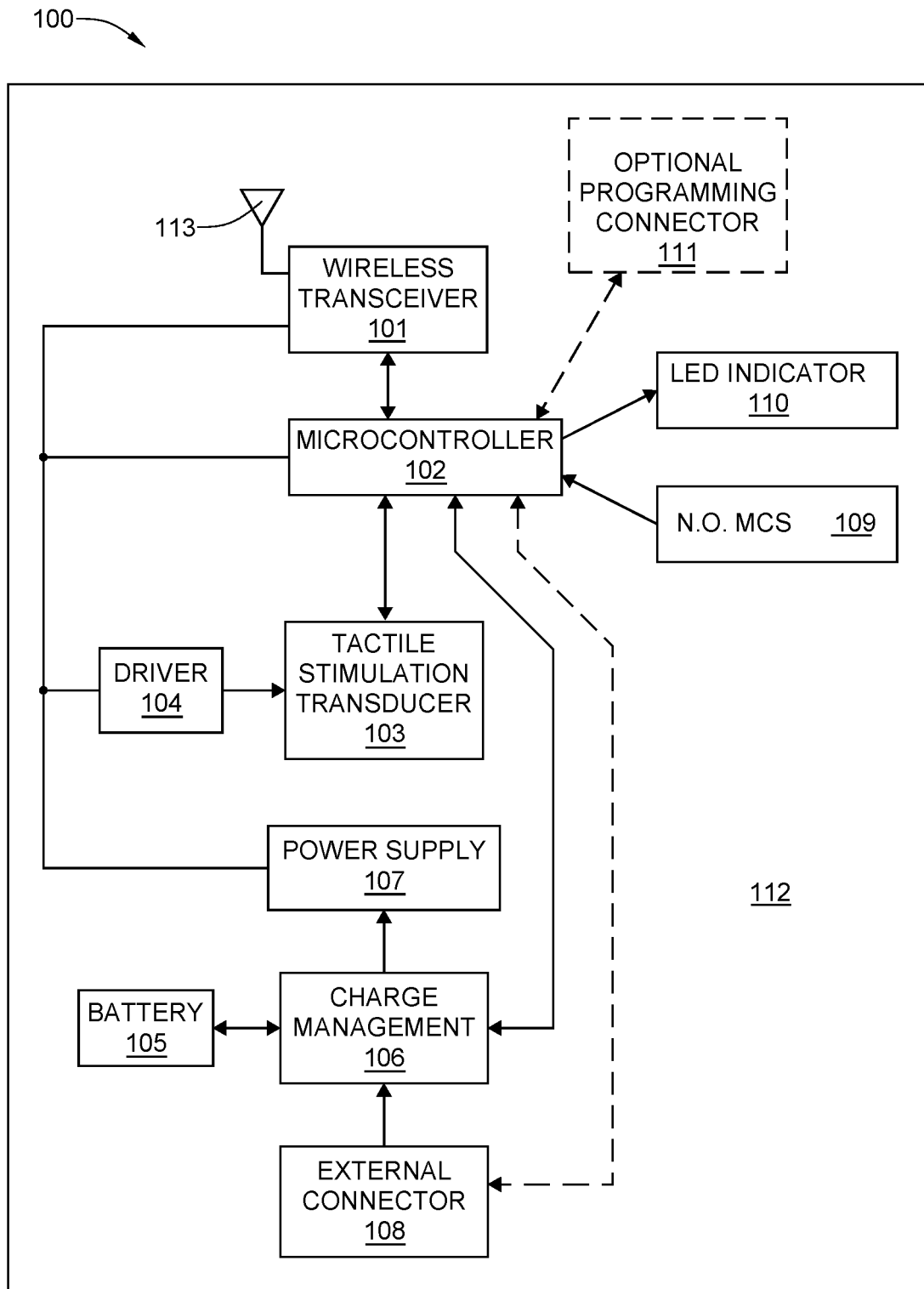
FIG. 1 is a block diagram of a tapper.

Referring now to FIG. 1, a preferred embodiment tactile stimulation module (also referred to herein as a rapper) 100 of the apparatus for administering bilateral tactile stimulation to a human subject comprises a wireless transceiver 101, a microcontroller 102, a tactile stimulation transducer 103, a driver circuit 104 for driving the tactile stimulation transducer 103, a power supply 107, a battery 105, a charge management circuit 106, which manages charging of the battery 105, a user-accessible external connector 108, a control element which, in this case is a normally open momentary contact switch (N.O. MCS) 109, at least one status indicator LED 110, an optional programming connector 111, and an antenna 113, all of which reside in a housing 112. A tapper can be held in the hand or worn on the wrist or ankle, by means of a strap, or can be worn inside the clothing. Tappers can be worn on a strap around the waist or around the chest or other body parts. Although the tactile stimulation transducer 103 is controlled by the driver circuit 104, it may be desirable to have direct communication between the transducer 103 and the microcontroller 102. For example, it may be desirable for the microcontroller 102 to know the back emf produced by the transducer 103. The tactile stimulation transducer 103 converts electrical energy, provided by the battery 105, into mechanical kinetic energy. When the tactile stimulation transducer 103 is energized by the driver circuit 104, electrical power is delivered, over time, to the tactile stimulation transducer 103, and that power is used to create mechanical motion.

Typically, the battery 105 is a secondary-type cell, which allows it to be recharged after it has become depleted. A presently preferred battery 105 uses Lithium-Iron-Phosphate (LiFePO4) chemistry. Other chemistries can be used, but the LiFePO4 is presently considered to be optimum in terms of power-density, cost and safety.

It is important to recharge the on-board battery according to a preferred charging profile for the chosen battery chemistry. The charge management block 106 performs this function for the battery 105. It regulates the rate of charge so as to not charge the cell too quickly, and it also limits the maximum charge to prevent over-charging the battery 105.

The power supply block 107 regulates, where necessary, the voltage to the various other blocks in the diagram of FIG. 1. The maximum output voltage of the battery 105 can be higher than the allowable input voltage of the microcontroller 102, the wireless transceiver 101, and the driver 104. Thus, the primary function of the power supply 107 is to provide regulated voltage to these blocks.

The external connector 108 enables the user to connect a cable to the tapper to recharge the battery 105. Optionally, the same connector 108 can be used to communicate with the microcontroller 102 for the purpose of reprogramming or setting registers or reading out data records. Substantially all of the connector is inside the housing 112, with only a portion of it being exposed. That portion which is exposed is an amount sufficient to connect an external charging/communication cable.

The wireless transceiver 101 facilitates wireless communication with other devices, such as another tapper or with a host device 203. The wireless transceiver 101 communicates with the microcontroller 102 digital data, typically using a universal asynchronous receive/transmit (UART) or serial peripheral interface (SPI) bus. The preferred embodiment for the wireless transceiver 101 supports at least one of the standard communication protocols found in the vast majority of host devices 203 available in the market. At this time the two primary wireless communication protocols are Bluetooth and Wi-Fi. The tappers typically use the Bluetooth protocol, and more specifically Bluetooth Low Energy (BLE) because of its optimized use of energy, which has the benefit of longer battery life than would generally be achieved by using Wi-Fi. In addition, most smartphones and tablet computers being sold today support the BLE protocol. Although a proprietary communication protocol could be used, there is likely no benefit to be derived from such use.

The tappers are designed to produce tactile stimulation that has the ability to substantially mimic human touch. In one embodiment, a vibratory motor having an unbalanced mass on its output shaft is driven with a very short pulse of energy, which causes it to activate briefly. As it is activated, the mass is accelerated as electrical energy is transformed into mechanical energy. As the mass undergoes acceleration, a force is exerted on the structure supporting the motor, according to Newton's laws. This force is ultimately conducted to the skin of the individual and the nerve endings thereunder. The characteristics (amplitude, duration, slew-rate, polarity, etc.) of the electrical pulse are tuned to produce a force that mimics human touch.

The tactile stimulation transducer 103 converts electrical energy into mechanical kinetic energy. When it is energized by the driver circuit 104, electrical power is delivered, over time, to the tactile stimulation transducer 103, and that power is used to create mechanical motion.

The driver 104 receives the vast majority of the energy, which it delivers to the tactile stimulation transducer 103, from the power supply 107 with only a negligible amount energy coming from the microcontroller 102. The microcontroller 102 simply provides a control signal to the driver 104. For strong tapping sensations, the driver delivers a relatively large amount of energy to the tactile stimulation transducer 103. The person experiences strong sensations of touch. For a gentle tap, a much smaller amount of energy is delivered to the tactile stimulation transducer 103, causing its shaft to rotate just a few revolutions. The energy can be delivered to the tactile stimulation transducer 103 in a variety of ways.

For the most intense sensation, the tactile stimulation transducer 103 is driven by the driver 104 at full voltage and full current in a DC-wise fashion.

For intermediate sensations, the tactile stimulation transducer 103 is driven by the driver 104 in a pulse-width-modulated (PWM) fashion at a relatively high PWM frequency. The tactile stimulation transducer 103 effectively low-pass-filters the PWM waveform produced by the driver 104 that is driving it. The duty-cycle of the PWM can be adjusted to effectively produce variable speed rotation of the tactile stimulation transducer 103.

For the gentlest tap, a very small amount of energy is delivered to the tactile stimulation transducer 103 by the driver 104 using a single, short-duration pulse, which causes the shaft to rotate a fraction of a full revolution.

An additional technique can be used to augment the gentle tap. A second single, short-duration pulse with reversed polarity can be applied to the tactile stimulation transducer 103, effectively braking it. In other words, the first pulse with forward polarity accelerates the tactile stimulation transducer 103. Substantially immediately following the first pulse, a second pulse with reverse polarity is applied to the tactile stimulation transducer 103, causing it to decelerate quickly instead of coasting to a stop.

In all three driving regimes, operation of the driver circuit 104 is entirely controlled by the microcontroller 102. The microcontroller 102 receives its power from the power supply 107. It is the core component of the entire tapper. Timing of the tactile stimulation transducer 103 is provided by the precise timing device onboard the microcontroller 102, which most likely is a crystal oscillator. During the period of time when the tapper is not being used by an individual, the microcontroller 102 minimizes energy consumption by causing the tapper to enter a low-power sleep mode, in which the amount of energy consumed from the battery 105 by the other blocks in the diagram of FIG. 1 is minimized to the greatest extent possible. The result is that the battery 105 will not discharge quickly while it is not in use. When the user presses the control element 109 the tapper 210 turns on and gives the user visual feedback through the LED 110. The user can also receive feedback via the tactile stimulation transducer 103. The microcontroller 101 can be programmed via the optional programming connector, or header 111. Alternatively, it can be programmed via the external connector 108. The preferred embodiment, for programming, however, is to program it over-the-air (OTA), or wirelessly through the wireless transceiver 101. OTA programming eliminates the need to disassemble the device to gain access to the optional programming header 111 and eliminates the need to connect a cable to the external connector 108. The microcontroller 102 provides the control signal to the driver circuit 104.

Figure 2:
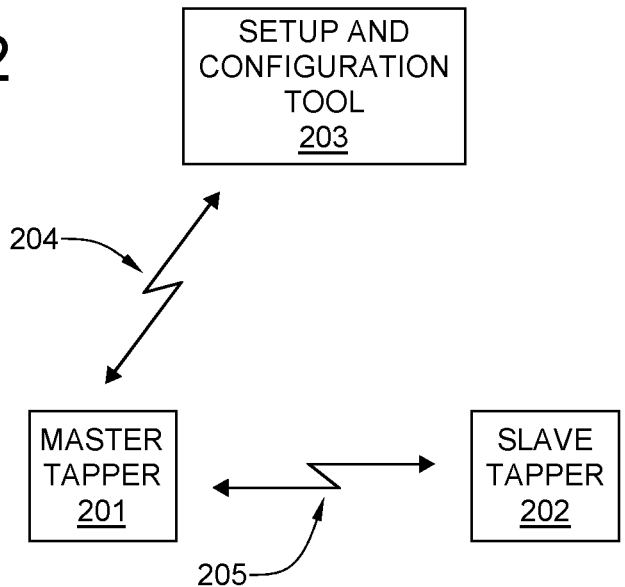
FIG. 2 is a block diagram of a master tapper, a slave tapper and a wirelessly connected host device, which functions as a setup and configuration tool.

Additional aspects of the invention are shown in FIG. 2. A host device 203 (also called a setup and configuration tool, or S&CT), such as a smart-phone or tablet computer, provides a source of wireless communication with a first tapper 201, which the host device 203 designates as the master. The first tapper 201 can, then, communicate wirelessly with a second tapper 202, which acts as a slave to the first tapper 201, without the host device 203 being involved. Alternatively, the host device 203 can exercise real time control over both tappers 201 and 202 during therapy sessions, with both tappers 201 and 202 being slaves of the host device 203. In the preferred embodiment, the means of wireless communication utilizes Bluetooth or Bluetooth Low Energy (BLE) protocol. The host 203 runs a user application, or app, that facilitates the setup and configuration of the tappers 201 and 202. Stimulation is applied in an alternating fashion by the first tapper 201 to one side of the person, then by the second tapper 202 to the other side, cycling back and forth between the tappers 201 and 202. The optimal rate of speed varies from person to person as does the intensity. While some individuals prefer or require a relatively intense stimulation, others experience maximum benefit from relatively mild stimulation. The rate at which the bi-lateral stimulation cycles back and forth influences the effectiveness of the therapy. The optimal rate varies from person to person and can even vary for a given person depending on their physiological conditions at the time the therapy is taking place. In addition to the rate that the bi-lateral stimulation is applied, the intensity with which it is applied also influences the effectiveness of the therapy. While some individuals prefer or require a relatively intense stimulation to get the maximum benefit from the therapy, other individuals experience maximum benefit from relatively mild stimulation. The host 203 allows the user to set the rate, intensity, and duration of the stimulation that the tappers 201 and 202 provide. The host 203 can be programmed to provide a number of optional parameters, such as ramping motor speed during turn-on and turn-off sequences. The shape of the ramping operation can be linear with variable slope, logarithmic, exponential and piece-wise linear.

Figure 3:
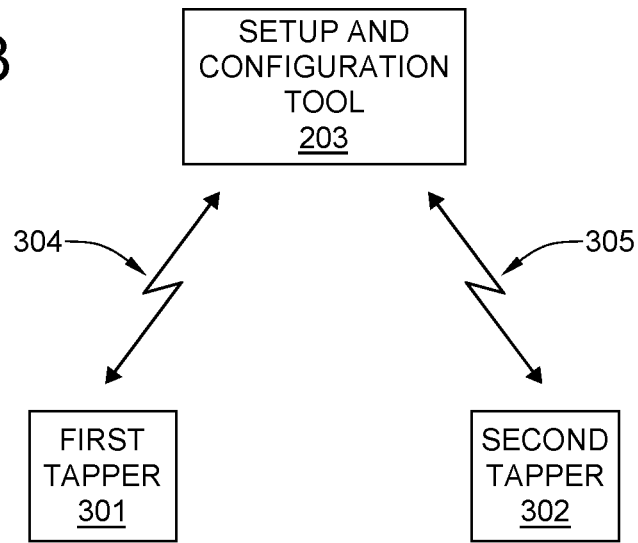
FIG. 3 is a block diagram of a first tapper and a second tapper, both of which are wirelessly-connected to the host device, which functions as a setup and configuration tool.

Referring now to FIG. 3, an alternate embodiment of the tapper system is shown where the host device 203 communicates wirelessly with both the first tapper 301 and the second tapper 302 through wireless communication signals 304 and 305, respectively.

Figure 4:
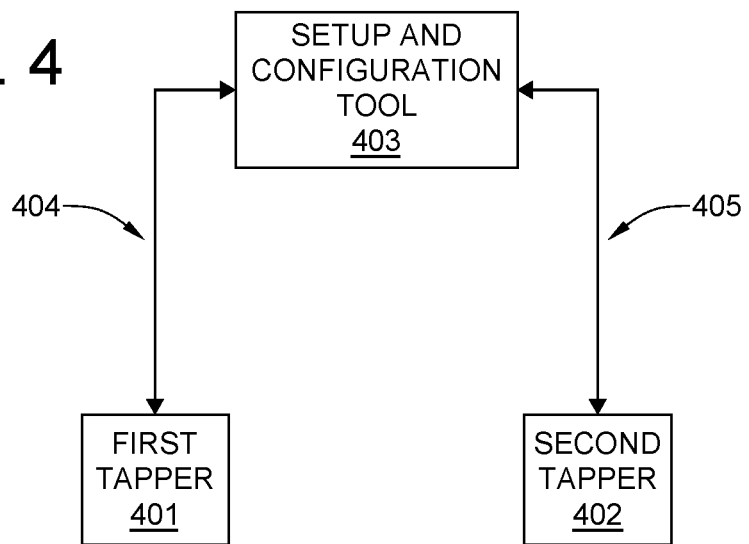
FIG. 4 is a block diagram of a first tapper and a second tapper, each of which is connected to the host device via an electrical cable.

Referring now to FIG. 4, a first alternate embodiment tapper system is shown where the host device 403 is connected to first tapper 401 and second tapper 402 with first and second electrical cables 404 and 405, respectively. The tappers 401 and 402 are not directly interconnected. The wires have the ability to provide power to the tappers from the host for the purposes of both charging the batteries in the tappers and to provide power to the tappers for operation. The cables 404 and 405 also have the ability to communicate with the tappers for the purpose of configuring the rate, intensity, and pulse duration parameters of the tappers.

Figure 5:
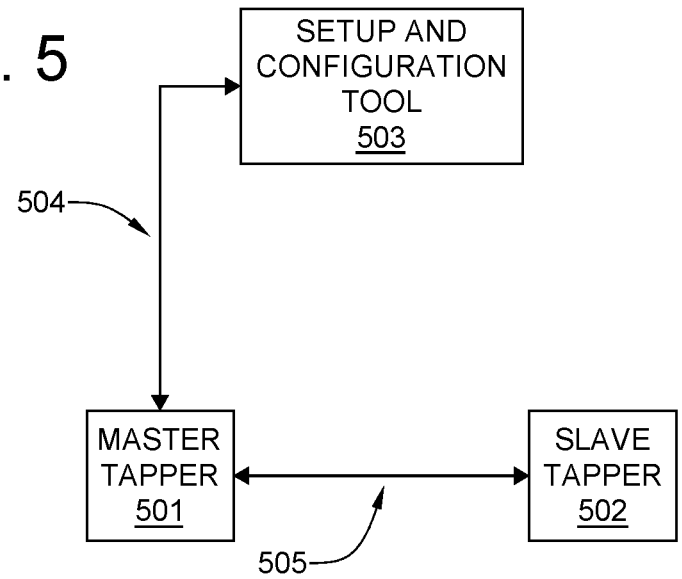
FIG. 5 is a block diagram of a master tapper and a slave tapper in which only the master tapper is connected to the host device via a first electrical cable, and the slave tapper is connected to the master tapper via a second electrical cable.

Referring now to FIG. 5, a second alternative embodiment tapper system is shown where the host device 502 is connected to a master tapper 501 via a first electrical cable 504, and the master tapper 501 is connected to a slave tapper 502 by a second electrical cable 505. The electrical cables 504 and 505 have the ability to provide power to the tappers from the host for the purposes of both charging the batteries in the tappers and to provide power to the tappers for operation. The cables also have the ability to communicate with the tappers for the purpose of configuring the rate, intensity, and duration parameters of the tappers.

Referring now to FIG. 6, after a master tapper 601 and a slave tapper 602 have been initially configured with a host device 502, they can operate autonomously without further connection to the host device. The tappers 601 and 602 remain synchronized and in cadence with each other by communicating wirelessly with one another via radio link 603.

Referring now to FIG. 7, an alternate embodiment of FIG. 6 depicts a master tapper 701 and slave tapper 702, which operate autonomously, after having been initially configured with a host device 203, using a wired connection 703 to maintain synchronization and cadence.

Referring now to FIG. 8, a preferred embodiment 103-A of the tactile stimulation transducer 103 of FIG. 1 comprises an electric motor 801 having a rotating balanced mass 802 attached to the rotating output shaft 803 of the motor 801. The combined motor armature, shaft and attached mass have what is known in physics as a moment of inertia. The moment of inertia, which is also known as rotational inertia, is a property of any object which can be rotated. It is a scalar value which indicates how difficult it is to change the rotational velocity of the object around a given rotational axis. In this case, the rotational axis would be the motor's axis of rotation. Rotational inertia plays a role in rotational mechanics that is similar to that of mass in linear mechanics. Indeed, the rotational inertia of an object depends on its mass, as well as the distribution of that mass relative to the axis of rotation. As a mass is moved further from the axis of rotation it becomes increasingly more difficult to change the rotational velocity of the system. Intuitively, this is because the mass is now carrying more momentum with it around the circle (due to the higher speed) and because the momentum vector is changing more quickly. Both of these effects depend on the distance of the mass from the axis. Rotational inertia is given the symbol I. For a single body having a mass m rotating at radius r from the axis of rotation, the rotational inertia is I=mr2. Consequently, rotational inertia has SI units of kg-m2. When the tactile stimulation transducer 103-A of FIG. 8 is used in a tapper 100, a tap can be generated by rotationally accelerating the motor armature, shaft 803, and balanced mass 802, as well as by braking rotation of the armature, shaft, and mass. If the motor 801 is properly balanced, the tactile stimulation transducer 103-A will not vibrate or buzz, no matter how long in duration an electrical pulse is applied to the motor inputs. When a full-power electrical pulse is applied to the electrical inputs of the motor 801, and as long as the motor shaft, armature and attached mass are accelerating, torque is being applied to the motor armature and balanced mass on the output shaft, resulting in an opposite and equal reverse torque being applied to the stator coils, motor housing and the motor support structure (i.e., nearly the entire tactile stimulation module), in accordance with Newton's laws. As the tapper 100 is pressed against the body of the individual undergoing tactile stimulation therapy, this opposite and equal reverse torque is perceived as a primary tap by the individual as it is conducted to the individual's skin and nerve endings thereunder. If the motor armature and attached balanced mass are slowed quickly, the rotational inertia is transferred to the motor stator, motor housing and the motor support structure, resulting in a secondary tap in the rotational direction of the armature. Such a technique has the potential for reducing power consumption of the device, especially if regenerative braking is used. Alternatively, the motor armature and attached balanced mass can be slowed more gradually so that no secondary tap is perceived by the holder or wearer of the device. The specific techniques of driving the tactile stimulation transducer 103 with the driver 104 can result in a variety of sensations experienced by the person. The majority of people undergoing tactile stimulation therapy require only gentle "taps" from the tappers 100. Such gentle taps can be achieved through short power pulses delivered to the motor 801 and gentle braking of the rotating armature, shaft 803, and mass 802. Other people who suffer from desensitized nerves, may require significantly more intense bilateral tapping from the tappers 100. Such intense tapping can be achieved through the use of power pulses of longer duration. The microcontroller of the tappers 100 may include programming that may enable the driver circuit 104 to operate with optional parameters, such as ramping motor speed during turn-on and turn-off sequences. The shape of the ramping operation can be linear with variable slope, logarithmic, exponential and piece-wise linear. Such capability can enable the tactile stimulation transducer 103 to induce a broad spectrum of sensations to the user.

Referring now to FIG. 9, a first alternative embodiment 103-B of the tactile stimulation transducer 103 of FIG. 1 comprises an electric motor 901 having an unbalanced mass 902 attached to the rotating output shaft 903 of the motor 901. Using this device, a tap can be generated, as heretofore explained, by rotationally accelerating the motor armature and unbalanced mass 902. Although use of an electric motor 901 having an unbalanced mass 90s attached to the rotating output shaft 903 of the motor 901 is not of a design that is optimum for producing a tapping sensation, the use of such motors is advantageous, if only because they are readily available and can be purchased at low cost. Because the rotating unbalanced weight on the vibratory motors acts as a very effective energy sink that causes the motor to coast quickly to a halt, there is little need to apply braking to such a motor. Buzzing, or vibration, which is an unwanted artifact of the motor design, can either be eliminated or severely minimized by shortening the duty cycles of the motor so that the armature is accelerated through no more than one full revolution, or 360 degrees and, preferably, through no more than one half revolution, or 180 degrees. Thus, when full power is applied to the motor electrical inputs and torque is applied to the armature, shaft 903 and unbalanced mass 902, an opposite and equal reverse torque is applied to the motor coils, motor housing, and the structure supporting motor, in accordance with Newton's laws, just as with the non-vibratory motor 801 of FIG. 8. The reverse torque is perceived by the user as a single tap. That opposite and equal force is conducted to the skin of the individual and the nerve endings thereunder. With the acceleration of the motor armature limited to no more than 360 degrees, only one vibrational pulse, at most, is driven, and that pulse will be contemporaneous with the reverse torque pulse. Thus, a person undergoing therapy will perceive the reverse torque force and the no more than one driven vibrational pulse, as a single tap. Given that an off-balance motor operates as an effective energy sink, with rotational energy being rapidly converted to vibrational energy, any residual vibrational energy decays rapidly as soon as the power pulse ends. At the high end of the 360-degree driven range, the decaying vibration is, of course, more noticeable. Thus, if the armature of an off-balance motor is driven through no more than 360 degrees, and especially through no more than 180 degrees, there will be little or no perception of vibration, thereby enabling the motor 901 to function, in most respects, in a manner that is virtually identical to that of the motor 801 that is equipped with a balanced mass on its output shaft. In addition, rotation of the motor armature can be braked as heretofore described for a motor with the balanced mass affixed to the output shaft. Thus, a tapping sensation can thus be achieved with either type of motor (balanced or unbalanced), although operating parameters must be more restrictive when using an unbalanced vibratory motor if noticeable vibration is to be avoided.

Still referring to FIG. 9, the greater the torque output and the greater the moment of inertia of the vibratory motor 901, the shorter the duration of a power pulse that will be required to produce a desired reverse torque that is perceived as a tap. Therefore, a discussion of desired power pulse widths is meaningful only if the moment of inertia (rotational inertia) and the torque rating of the unbalanced vibratory motor are known. A current embodiment tapper utilizes a vibratory motor 901 having a relatively large moment of inertia, a relatively high torque rating, and a rotational speed of 12,000 rpm (1 revolution every 0.005 seconds) under full power. That means that, if full motor speed were achieved with full power applied to the inputs for 10 milliseconds (highly unlikely) and acceleration were linear, the armature would be accelerating under power for only half a revolution during a power pulse of 5 milliseconds duration. With this motor, reverse torque pulses that are perceived as the tap of a human finger can be generated with full-power pulses applied to the motor inputs that have a duration within a range of about 92 microseconds to about 5 milliseconds. Although pulses of up to 10 milliseconds are still perceived as a tap, when the pulses exceed much over 10 milliseconds in duration, multiple vibrational pulses are being generated as the motor armature coasts to rest, and that decaying vibration becomes more noticeable. The greater the motor speed and the greater the number of revolutions, the more intense the vibrational sensation experienced by a user of the device. Consequently, use of a vibratory motor limits design flexibility, as driven vibration can become the dominant forces experienced by the user. Because an off-balance vibratory motor generates vibrations as it rotates at full speed, the production of a secondary tap caused by rapid braking of the motor armature and unbalanced mass would be accompanied by constant driven vibration between taps. Because this is not a desirable scenario, taps produced by a vibratory motor having an unbalanced mass affixed to its output shaft should be limited to primary taps produced by the reverse torque of motor startup.

Referring now to FIG. 10, a second alternative embodiment 103-C of the tactile stimulation transducer 103 includes an electric pump 1001 and a bladder 1002. The pump 1001 inflates and deflates the bladder 1002 in such a way as to mimic the tap of a human hand. The speed of the electric pump 1001 can be varied in order to increase or decrease the intensity of the tapping sensation.

Referring now to FIG. 11, a third alternative embodiment 103-D of the tactile stimulation transducer 103 employs a scissor jack method of tactile stimulation. A solenoid 1101 has a linearly reciprocating output shaft 1102 that is coupled to a scissor-jack 1103. By maintaining pivot 1104 stationary, the scissor jack expands and flattens with the back and forth movement of the output shaft 1102.

Referring now to FIG. 12, a fourth alternative embodiment 103-E of the tactile stimulation transducer 103 includes a linear actuator 1201, which has a pressure plate 1203 secured to a reciprocating output shaft 1202. The moving pressure plate 1203 is pressure coupled to the body of the person receiving therapy.

For the third and fourth alternative embodiments 103-D and 103-E, respectively, of the tactile stimulation transducer 103, the physical properties of the power pulses sent to the solenoid 1101 and the linear actuator 1201 can be modified with respect to amplitude, duration, slew rate and polarity in order to change the characteristics of the tapping sensation that those devices produce.

Figure 13:
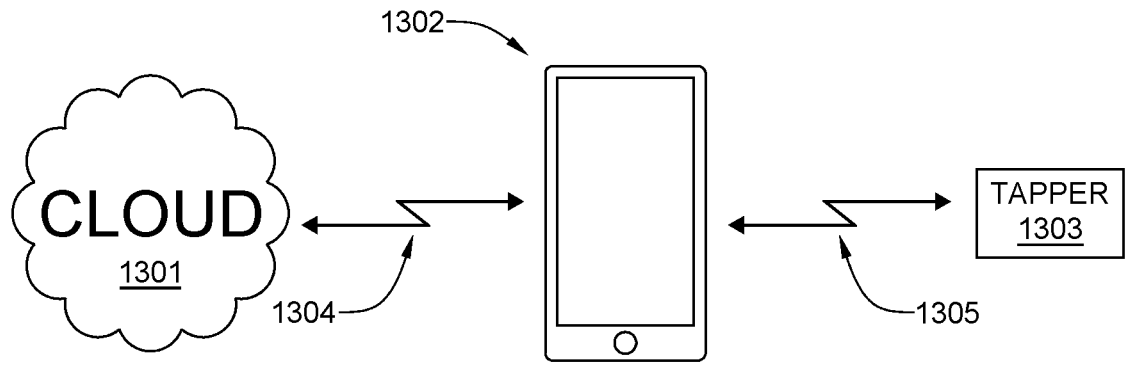
FIG. 13 is a block diagram showing the updating of firmware of a host device and of a tapper from firmware images stored on a cloud-based server accessible via the Internet.

Referring now to FIG. 13, an important part of the invention is to incorporate the ability to update the computer code, or firmware, running in both the host device 1302 and the tappers 1303. In order to affect the update, the host device 1302 communicates with the cloud 1301 typically via a Wi-Fi connection or via a cellular connection. The host 1302 is able to download updated versions of the firmware for itself and for the tappers 1303. The firmware running in the host 1302 is typically referred to as an application or, simply, an app. The firmware in the tappers 1303 is updated by the host 1302, after the host 1302 has downloaded the updated firmware for the tapper 1303 from the cloud 1301. The host 1302 wirelessly transfers the updated version of firmware to the tappers 1303. A verification process is enacted, which ensures that the firmware in both the host 1302 and in the tappers 1303 has been successfully installed.

Figure 14:
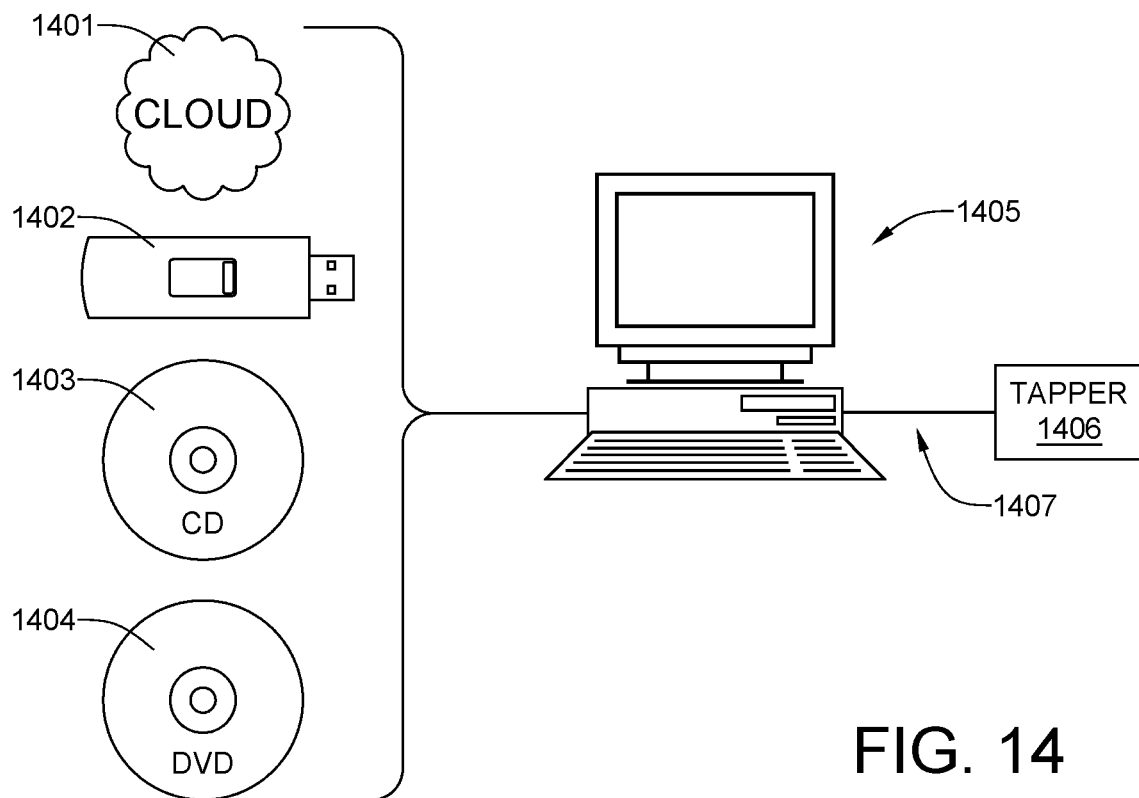
FIG. 14 is a block diagram showing the updating of firmware of a host device and of a tapper via a wired connection to a personal computer using firmware updates from a variety of sources, including the cloud, a USB flash drive, a compact disc and a digital video disc.

Referring now to FIG. 14, various other methods of updating firmware, employing a personal computer 1405, are shown. The firmware can be downloaded from the cloud 1401, read from a flash drive 1402, from a compact disc (CD) 1403, or from a digital video disc (DVD). A firmware update program running on the personal computer 1405 manages the firmware update to the tappers 1406.

Another important part of the invention relates to the flexibility of how contact between the tappers and the individual is maintained. A person may hold a tapper in each hand, without the aid of a strap or other retention device. Likewise, a tapper may be held in place against the skin by an individual's clothing. For example, each tapper may be held in place against the ankle or calf by a sock or compression sleeve, or against the wrist or forearm with a glove or compression sleeve. Each tapper may be worn on a wrist of the individual by means of a watch-band-like strap associated with each tapper. This embodiment will be shown extensively in the attached drawing FIGS. 18 through 30.

Figure 15:
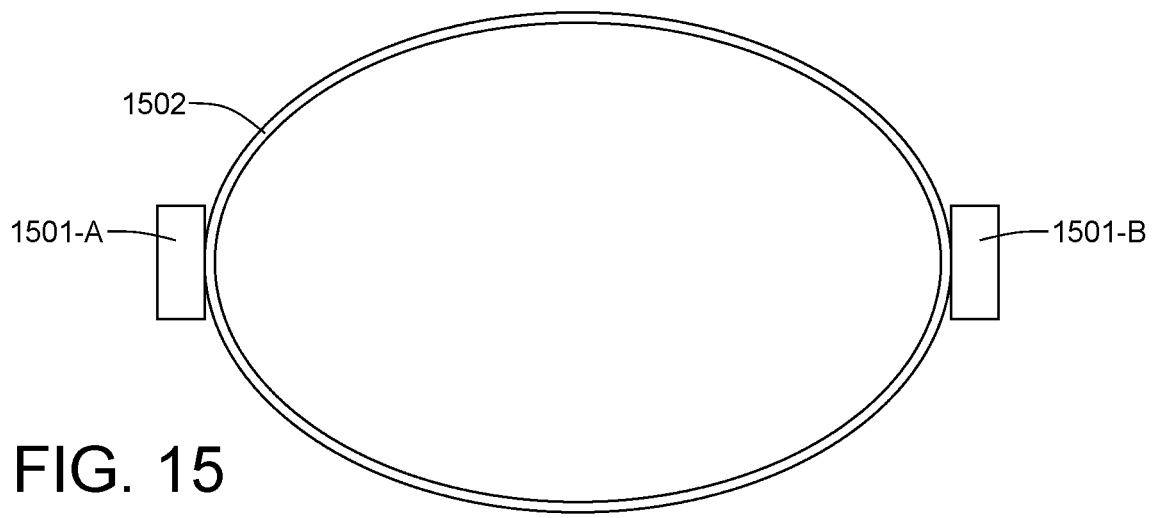
FIG. 15 is a block diagram of a pair of tappers attached to a band that is worn around the waist, worn on the head or worn around the chest.

Referring now to FIG. 15, a pair of tappers 1501-A and 1501-B are attached to a single band 1502, which can be worn about the head, chest, or waist so that the tapper is in sufficient proximity to the body that the individual can sense the tapping.

Figure 16:
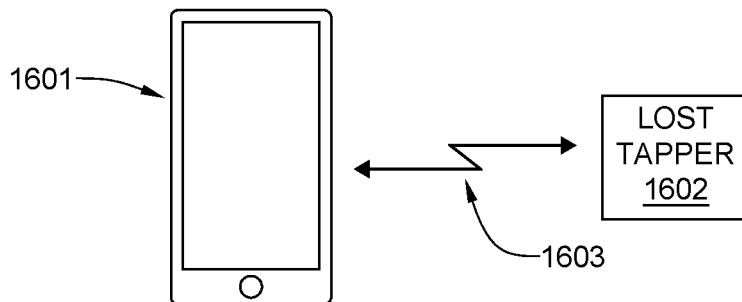
FIG. 16 is a block diagram that depicts a method for finding a lost tapper.

Referring now to FIG. 16, it is contemplated that an individual may inadvertently lose or misplace one or both tappers. So that an individual may find lost tappers, the host 1601 communicates wirelessly via radio signals 1603 with the lost tapper 1602. The host 1601 gives the user feedback as they get closer to or further from the lost tapper 1602, by analyzing the quality of the wireless link 1603 between the host 1601 and the lost tapper 1602, thereby enabling the individual to narrow the search area. When the lost tapper 1602 is sufficiently close to the host device 1601, the host device can direct the lost tapper to vibrate continuously until it is found by the individual.

Figure 17:
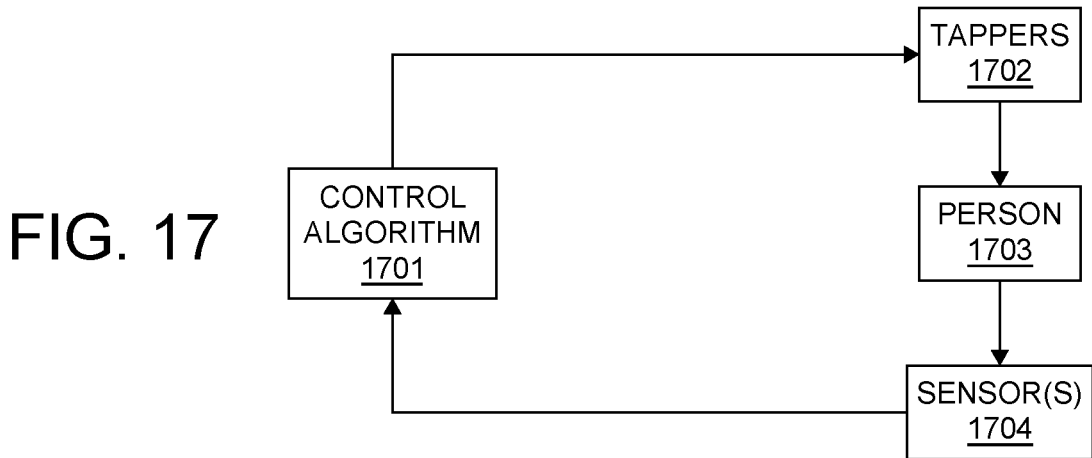
FIG. 17 is a block diagram which depicts a bio-feedback control system for tappers.
Figure 18:
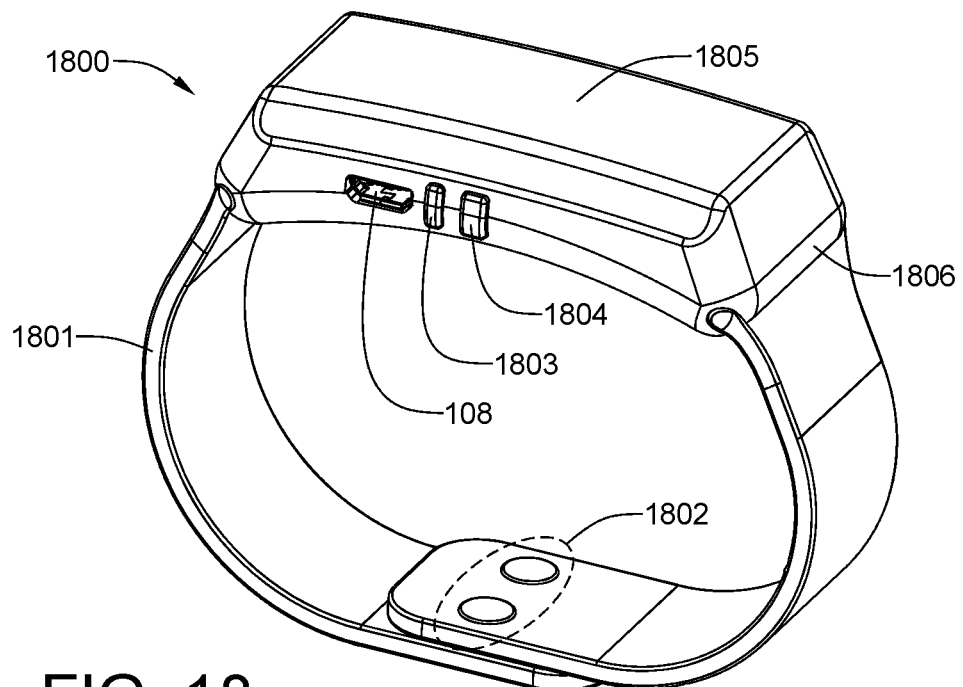
FIG. 18 is an isometric view from an elevated vantage point of a wrist-wearable tapper.
Figure 19:
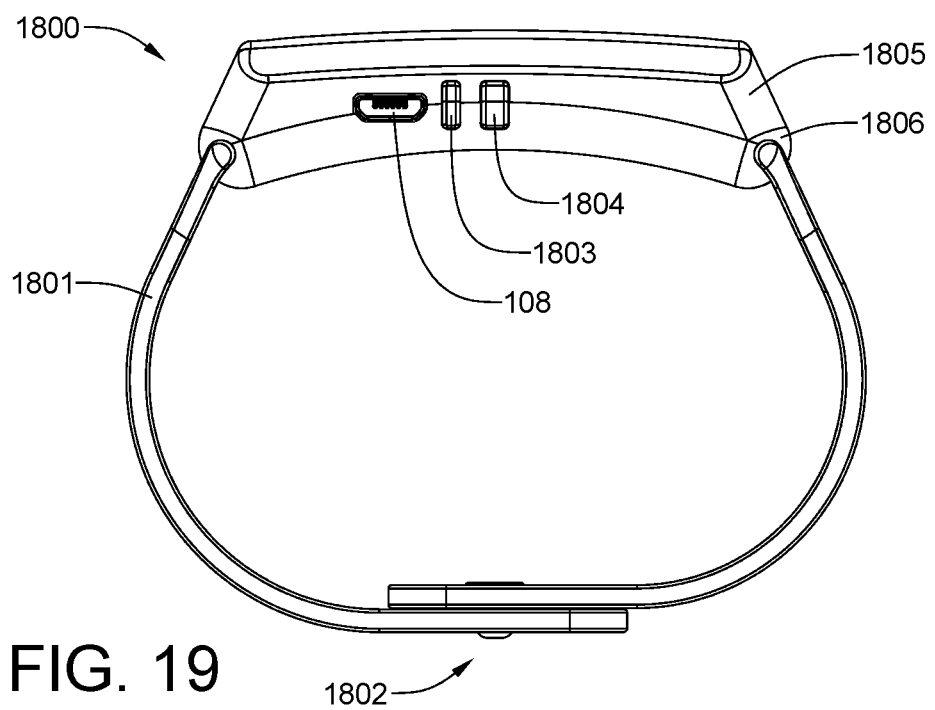
FIG. 19 is a front elevational view of the wrist-wearable tapper of FIG. 18.
Figure 20:
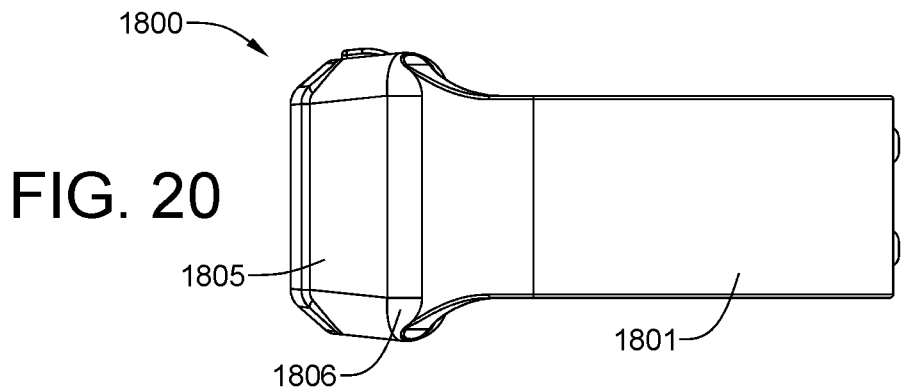
FIG. 20 is a left-side elevational view of the wrist-wearable tapper of FIG. 18.
Figure 21:
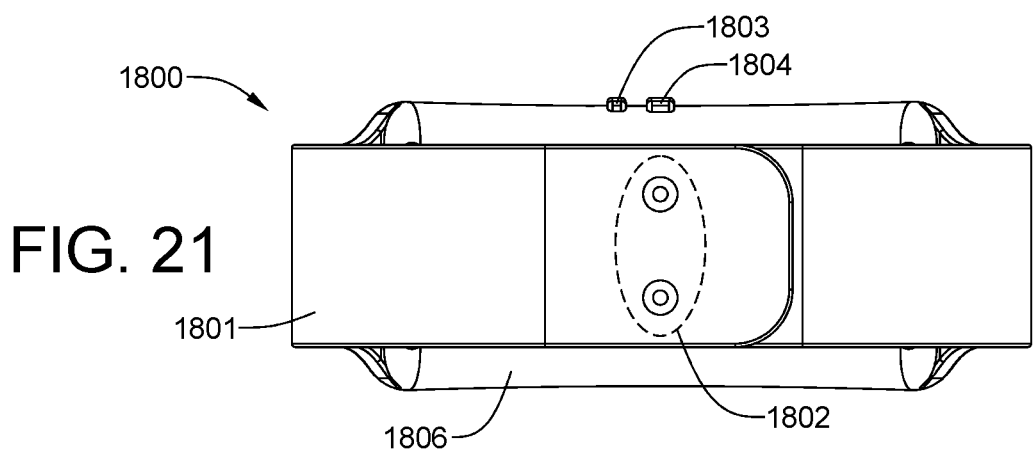
FIG. 21 is a bottom plan view of the wrist-wearable tapper of FIG. 18.
Figure 22:
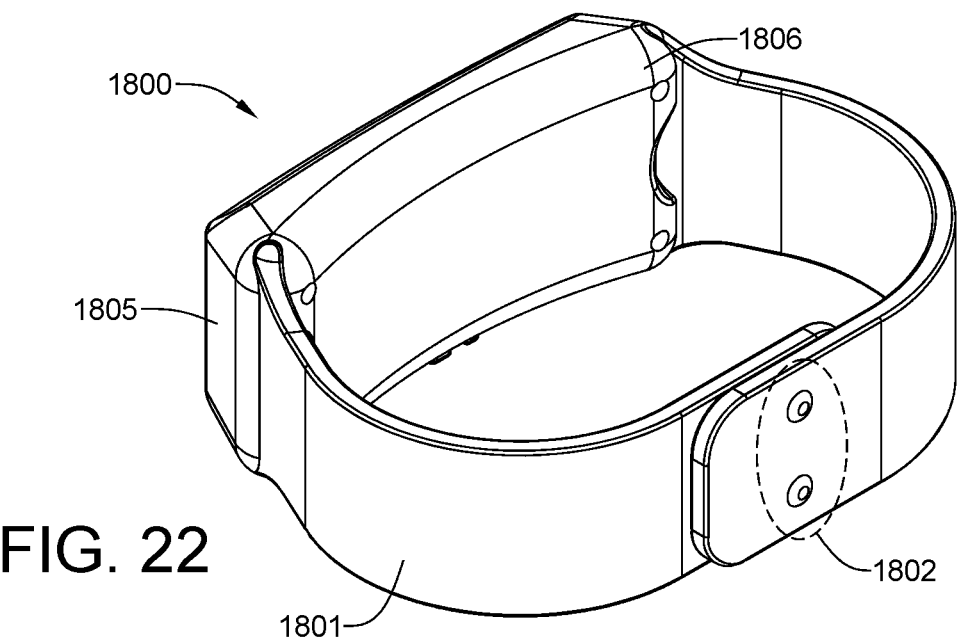
FIG. 22 is an isometric view from a lower vantage point of the wrist-wearable tapper of FIG. 18.
Figure 23:
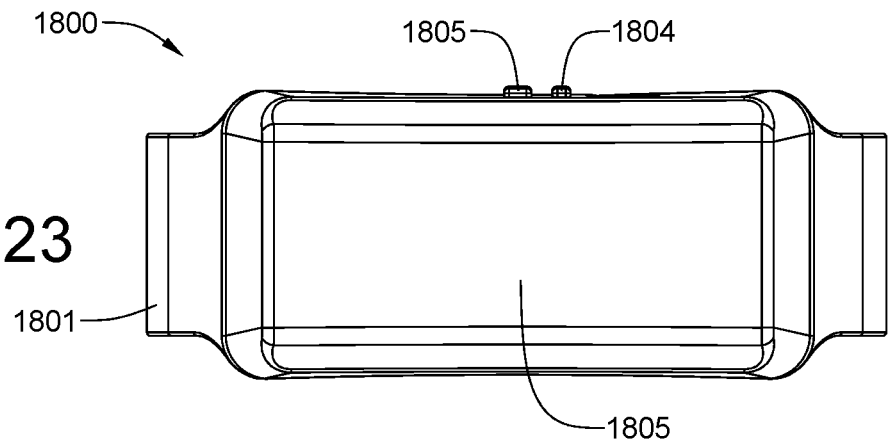
FIG. 23 is a top plan view of the wrist-wearable tapper of FIG. 18.
Figure 24:
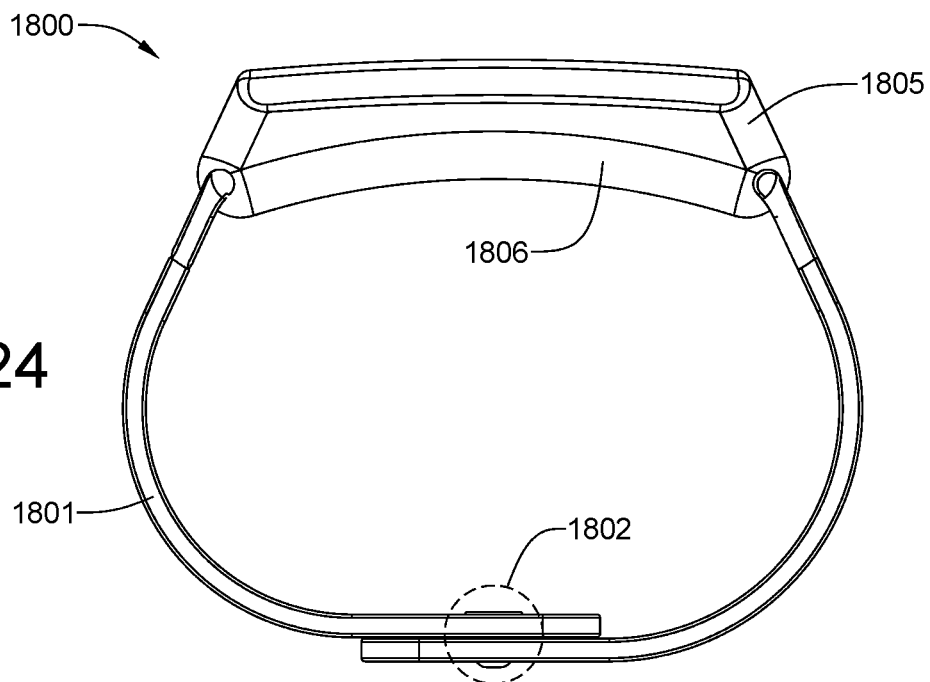
FIG. 24 is a rear elevational view of the wrist-wearable tapper of FIG. 18.

Referring now to FIG. 17, an embodiment of the tapping is shown in which bio-feedback is used to enhance the therapy. A bio-feedback system is shown that incorporates a pair of tappers, which are shown as a single block 1702 the person receiving the tapping therapy, and at least one sensor 1704 located either in at least one of the tappers or separate from the tappers, and a control algorithm 1701. These elements are part of a control loop in which the tappers 1702 stimulate the individual 1703, a bio-response, in the form of a measurement of a physiological function, is detected by the sensor(s) 1704, and the control algorithm 1701 performs an analysis of the bio-response and implements a slightly adjusted control signal which is sent to the tappers 1702. This process repeats itself around the loop with the goal of driving the bio-response to a desired condition. Exemplary measurements of physiological functions include: Pulmonary (heart) rate; Respiratory (breathing) rate; Temperature; Muscle Activity using a surface electromyograph (SEMG); Skin Electrical Activity using an electrodermograph (EDG); Brain Electrical Activity at cortical sites using an electroencephalograph (EEG); Blood Flow in Fingers and Toes using a photoplethysmography (PPG); Heart Electrical Activity using an electrocardiograph with probes on ankles and wrists (ECG); Brain Blood Flow using a rheoencephalograph (REG); Oxygenation Levels of Blood in the Brain using a hemoencephalograph (HEG) by measuring infrared light image reflected from scalp (used to identify ADHD); Breathing Rate, Abnormal Breathing Conditions such as reverse, thoracic and clavicular using a pneumography; Exhaled CO2 Levels using a capnometer (used to identify states of anxiety, hypertension, and panic, as well as asthma); Heart Rate and Oxygen Saturation Levels in the Bloodstream using an oximeter; Muscle Tightness or Tension using a pressure sensor (indicative of tension).

Indications of sensor measurements may be displayed as bio feedback on the mobile device screen or an indicator on the sensor itself to help the user be more aware of his/her current condition so that he/she can learn to control thought processes that result in maintaining a state of greater calm.

The host or master device with which the tappers communicate wirelessly is typically a smart-phone or tablet computer, though other devices are contemplated. The host contains an application that allows the user to: adjust various therapy parameters in the tappers; start and stop therapy; and get status from the modules, such as battery charge status, gather usage data, etc.

For a presently preferred embodiment of the invention, the bio-response measured by the sensors 1704 is the heart rate of the person receiving therapy 1703. A person who is hyper-aroused typically exhibits a heart-rate above a certain threshold. When this is the case, the aim of the control loop is to encourage the heart rate to reduce to a slower cadence. Alternatively, a person who is hypo-aroused typically exhibits a heart-rate below a certain threshold. When this is the case, the aim of the control loop is to encourage the heart rate to increase to a faster cadence. The rate, duration, and other electro-mechanical aspects of the tappers 1702 can influence the bio-response of the person 1703 to either cause the heart rate to increase or decrease. Thus, it is an aim of the control algorithm 1701 to determine whether the heart rate should be encouraged to increase or decrease and provide an appropriate control signal to the tappers 1702 to effect the desired change.

The application operates in a "machine learning" mode, where the speed and intensity of the tapping are varied over a substantial range. Simultaneously, a human physiological function, such as heart rate, is measured. The human physiological function is mapped across the range of speed and intensity to locate the optimal point for the particular user. The process is repeated under varying circumstances (time of day, level of physical activity, time of year, different weather patterns, different physical locations such as home/work/school/driving/relaxing) to determine the optimal tapping speed and intensity for the particular user. The resulting set of optimal tapping speed and intensity is used as a starting point each time the product is activated. Even after an "optimal" value is found, the tapping rate and intensity may be varied by the software from time to time to see if the user's ideal settings have changed, helping to fine-tune the ideal settings on an ongoing basis. This machine learning can also be charted and/or tracked and a trend plot produced so the user can observe their physiological changes over time, and correlate the trends to events in their own lives.

Still referring to FIG. 17, for a preferred embodiment of the control algorithm 1701, the heart rate is measured. If the person 1703 is in a state of hyper-arousal and his heart rate is too rapid, then the tapper rate will gradually slow down, which encourages the heart rate of the person 1703 to gradually decrease. As the heart rate comes into an acceptable range, then the control algorithm causes the tapper rate to stabilize. Conversely, if the person 1703 is in a state of hypo-arousal, and his heart rate is too slow, then the tapper rate will gradually speed up, which encourages the heart rate of the person 1703 to gradually increase. As the heart rate comes into an acceptable range, then the control algorithm causes the tapper rate to stabilize. The bio-feedback control algorithm is designed to help a person achieve a deeper level of biostasis more rapidly and/or for a longer period of time.

The host has the ability to keep track of the usage of the tappers in a logfile. The therapist or the individual receiving treatment can retrieve the log-file, track progress and the therapist can make recommendations to the individual.

Referring now to FIGS. 18 through 24, a presently preferred embodiment of a tapper 1800 is configured with a commercially available wrist strap 1801 that is secured by a clasp 1802. The tapper 1800 utilizes a connector 108 for charging and communication. A status indicator lens 1803, which covers the status indicator LED 110, gives the user visual feedback as to the operational status of the tapper 1800. The status indicator LED may also be used to enhance EMDR therapy in an alternate embodiment. A button 1804 enables the user to turn the tapper on and off, and also facilitates additional user interactions with the tapper 1800. The tapper body has a top cover 1805, which fits over a base 1806.

Figure 25:
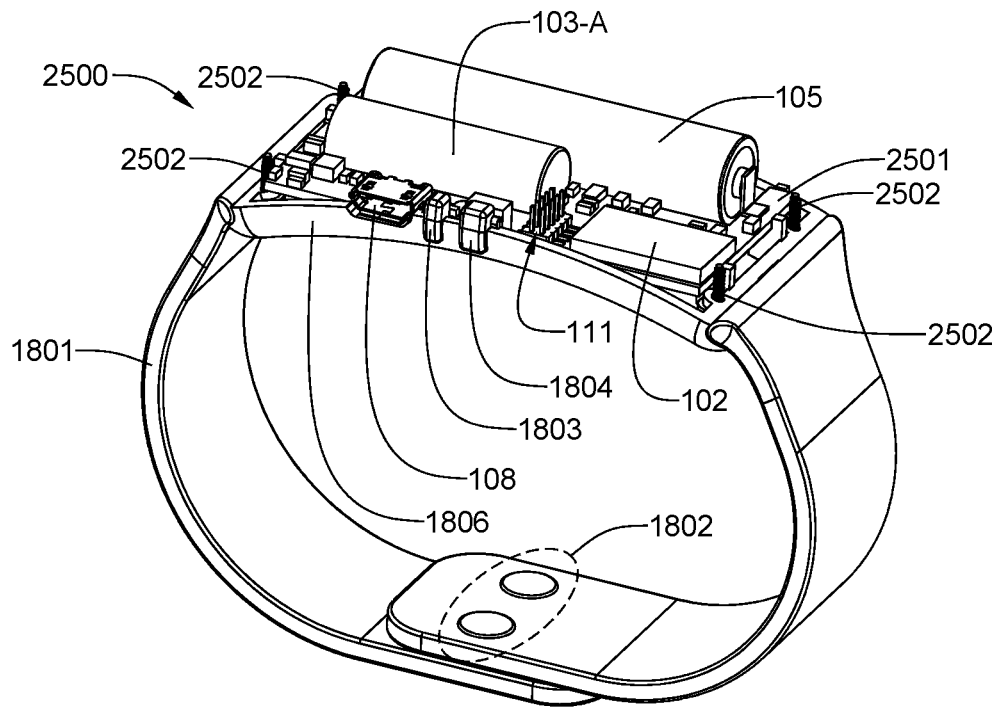
FIG. 25 is an isometric view of the tapper of FIG. 18, with the cover removed to show the internal components, which include an electric motor—having a balanced mass on its output shaft—installed in a cylindrical housing, taken from an elevated front vantage point.

Referring now to FIG. 25, a preferred embodiment tapper 2500 is shown with its top cover 1805 removed by loosening the screws 2502, thereby exposing the internal components of the tapper. A connector 108, an LED indicator 1803 and a button 1804 are visible in this view. The top cover 1805 has been removed to expose the interior components. A cylindrical tactile stimulation transducer 103-A is visible, which in this case incorporates an electric motor 801 having a balanced mass 802 secured to the motor output shaft 803. A battery 105 powers the tapper 2500. The battery 105 in the preferred embodiment is a lithium-iron-phosphate (LiFePO4) cell. Other battery chemistries are contemplated. The LiFePO4 is advantageous because it offers better volumetric and gravimetric energy density than NiCd and NiMH chemistries. LiFePO4 is also thought to present lower risk of fire than LiPo and Li-ion. The microcontroller 102 is also shown. A circuit board 2501 is secured to the inside of the tapper base 1806.

Figure 26:
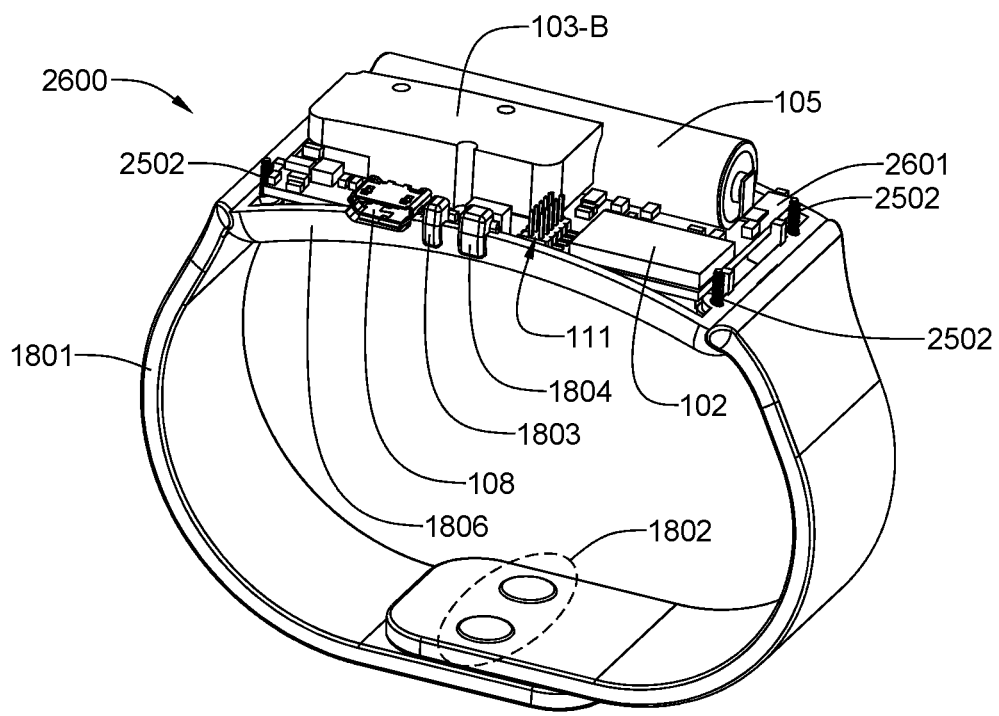
FIG. 26 is an isometric view of the tapper of FIG. 18, with the cover removed to show the internal components, which include an electric motor—with an unbalanced mass on its output shaft—installed in a rectangular housing, taken from an elevated front vantage point.

Referring now to FIG. 26, an alternative embodiment tapper 2600 is shown with its top cover 1805 removed by loosening the screws 2502, thereby exposing the internal components of the tapper. This alternative embodiment tapper 2600 is similar to embodiment 2500, with the exception that the tactile stimulation transducer 103-B is block shaped and incorporates an electric motor 901 having an unbalanced mass 902 secured to the motor output shaft 903. It should be mentioned that functionally equivalent stimulation transducers come in a variety of shapes. In order to accommodate the different tactile stimulation transducer 103-B, the circuit board 2601 has been modified slightly.

Figure 27:
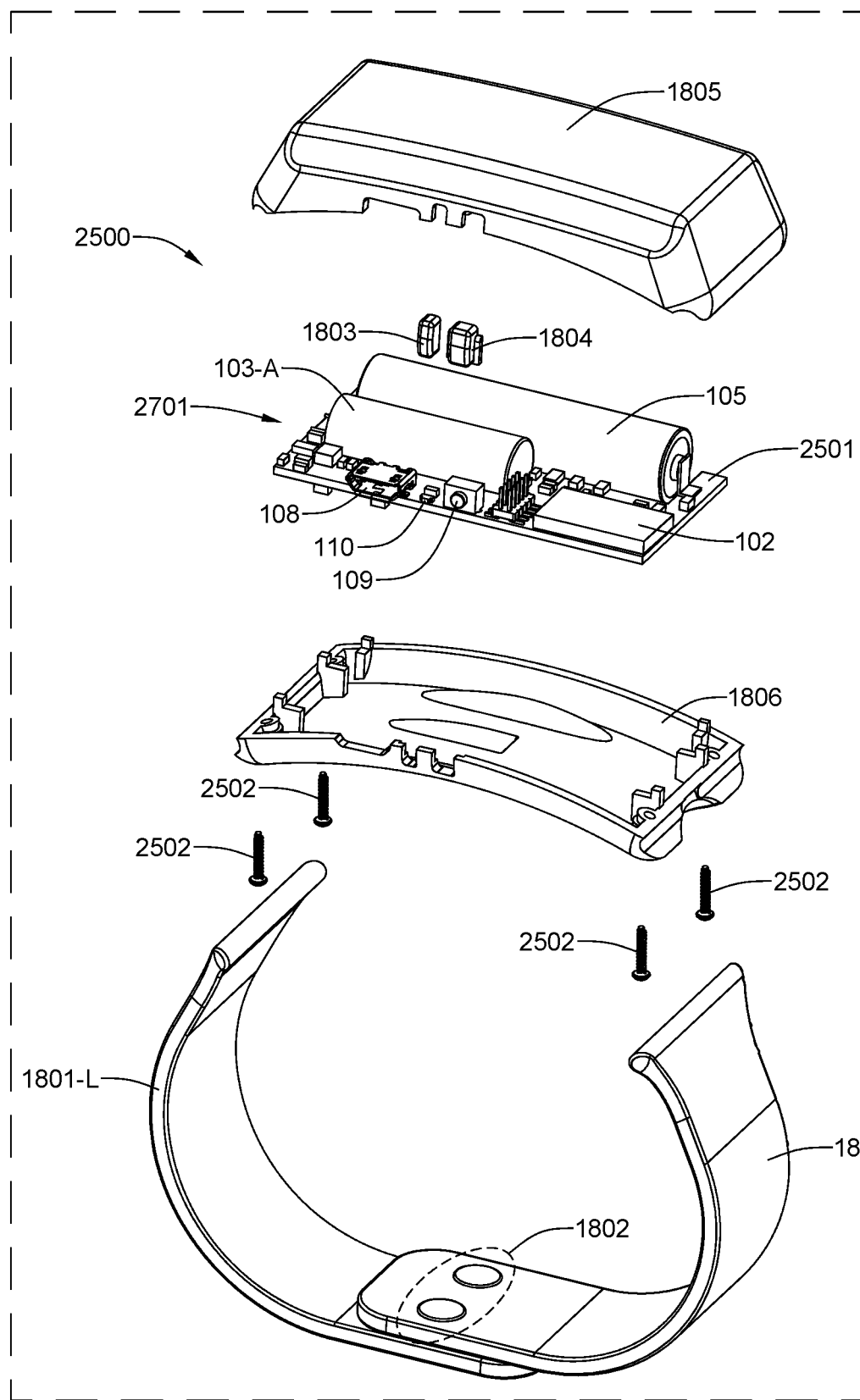
FIG. 27 is an isometric exploded view of the tapper of FIG. 25, taken from an elevated front vantage point.

Referring now to FIG. 27, the tapper 2500 of FIG. 25 is shown in an exploded view. The tactile stimulation transducer 103-A is secured to the circuit board 2501. The circuit board assembly 2701, with all components soldered to the circuit board 2501, has been removed from the base 1806. Thus, a preferred embodiment tapper includes a base 1806, a top cover 1805, a circuit board assembly 2701 incorporating a balanced-mass motor tactile stimulation transducer 103-A, a user pressable button 1804 that activates the normally-open momentary contact switch 109, and a status indicator lens 1803 that covers the status indicator LED 110. The entire tapper is held together with four self-tapping screws 2502. The wrist strap 1806 has an upper portion 1806-U and a lower portion 1806-L.

Figure 28:
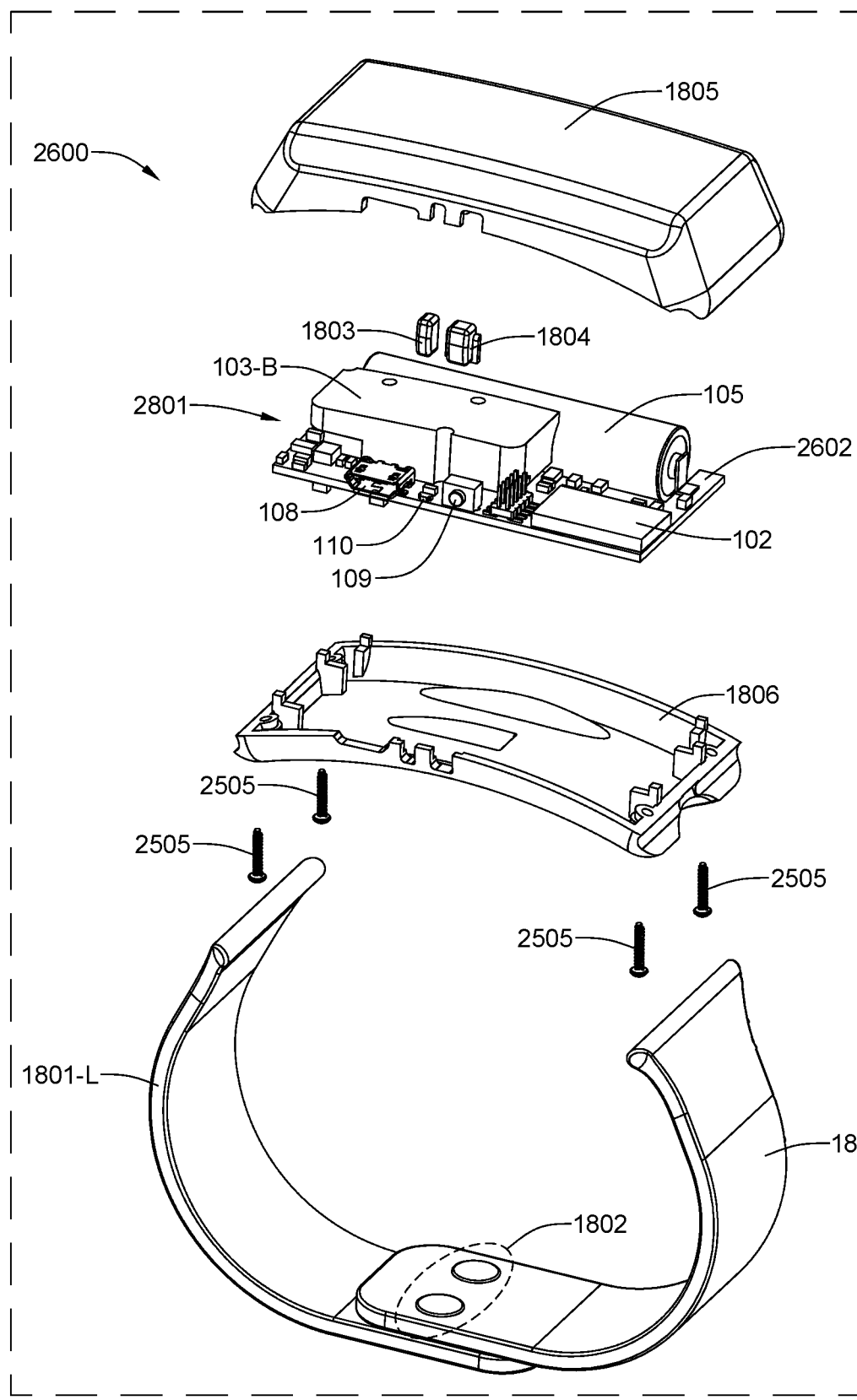
FIG. 28 is an isometric exploded view of the tapper of FIG. 26, taken from an elevated front vantage point.

Referring now to FIG. 28, the tapper 2600 of FIG. 26 is shown in an exploded view. This embodiment tapper 2600 is similar to the tapper 2500 of FIGS. 25 and 27, with the primary difference being substitution of an unbalanced mass motor tactile stimulation transducer 103-B for the balanced-mass motor tactile stimulation transducer 103-A.

Figure 29:
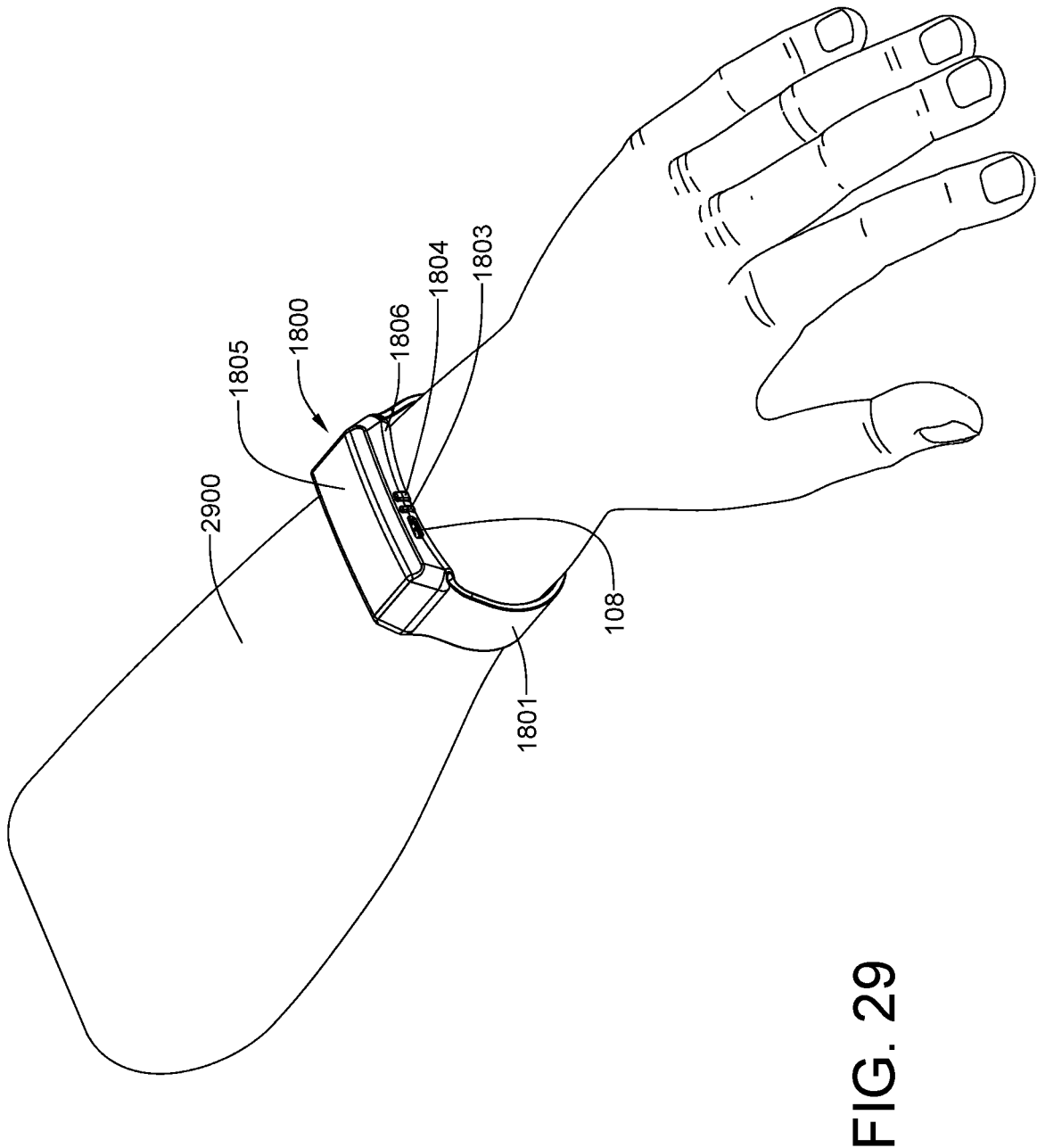
FIG. 29 is an isometric view of a tapper as worn on the left arm of a person.

Referring now to FIG. 29, a tapper 1800 is shown secured to an individual's arm 2900 with a commercially available wrist strap 1801.

Figure 30:
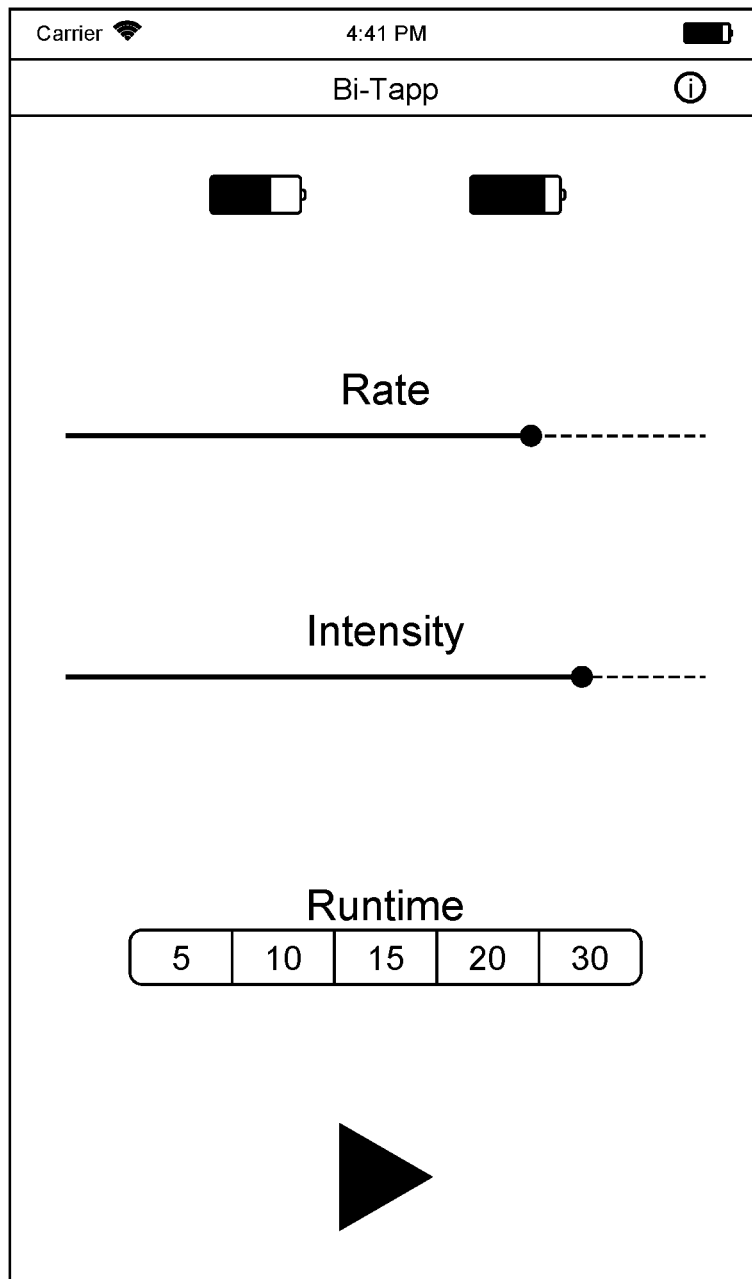
FIG. 30 is an example of the appearance of the application screen on the host.

Referring now to FIG. 30, an example of the appearance of the app on the host provides indication of the approximate charge status of the battery in each paired tapper. It also provides indication of the pairing status of each of two tappers. It allows the user to adjust the rate and intensity of the tactile stimulation in the tappers. It also allows the user to set the duration of a "tapping session". It also allows the user to start and stop the tapping.

Although only preferred embodiments of the apparatus for administering bilateral tactile stimulation to a human subject have been shown and described herein, it will be obvious to those having ordinary skill in the art that changes and modifications may be made thereto without departing from the scope and the spirit of the invention as hereinafter claimed.

What is claimed is:

1. A method of eliciting a calming effect on a human subject by using bilateral tactile stimulation, the method comprising:
    placing a tactile stimulation module in contact with the human subject, the tactile stimulation module powered by a battery and comprising an electric motor,
    wherein torque used to rotationally accelerate an output shaft of the electric motor generates an opposite and equal reverse torque that is applied to the tactile stimulation module and is perceived as a tap by the human subject; and
    activating the electric motor to apply the tap at a desired rate until the human subject is calmed.

2. The method of claim 1, further comprising measuring a physiological function of the human subject comprising one or more of a pulmonary rate, a respiratory rate, a temperature, a muscle activity, a skin electrical activity, a brain electrical activity, a blood flow, a heart electrical activity, exhaled $CO_2$ levels, a heart rate, oxygen saturation levels, and muscle tightness.

3. The method of claim 2, wherein the desired rate is determined and adjusted according to the measurement of the physiological function of the human subject.

* * * * *